United States Patent [19]

Takao et al.

[11] Patent Number: 4,840,957

[45] Date of Patent: * Jun. 20, 1989

[54] PYRAN DERIVATIVES

[75] Inventors: Hisashi Takao; Norio Osaki; Norio Yasudomi, all of Tokushima, Japan

[73] Assignee: Otsuka Kagaku Kabushiki Kaisha, Osaka, Japan

[*] Notice: The portion of the term of this patent subsequent to May 3, 2005 has been disclaimed.

[21] Appl. No.: 146,671

[22] Filed: Jan. 21, 1988

Related U.S. Application Data

[60] Division of Ser. No. 920,937, Oct. 20, 1986, Pat. No. 4,742,078, which is a continuation of Ser. No. 614,165, May 5, 1984, abandoned.

[51] Int. Cl.$^4$ .................. A01N 43/40; C07D 405/06
[52] U.S. Cl. .................. 514/326; 546/207; 544/96; 544/149; 544/333; 544/374; 548/215; 548/300; 548/517; 549/417; 514/374; 514/385; 514/422
[58] Field of Search .................. 546/207; 514/326

[56] References Cited

U.S. PATENT DOCUMENTS 4,742,078 5/1988 Takao et al. .................. 514/460

Primary Examiner—Glennon H. Hollrah
Attorney, Agent, or Firm—Armstrong, Nikaido Marmelstein Kubovcik & Murray

[57] ABSTRACT

A pyran derivative represented by a general formula

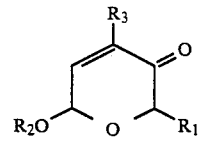

wherein $R_1$ is hydrogen, lower alkyl, cycloalkyl or phenyl, $R_2$ is alkyl having 8 to 20 carbon atoms, $R_3$ is hydrogen, halogen,

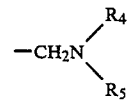

or $-CH_2N\overbrace{A}$, $R_4$ and $R_5$ being each lower alkyl or cycloalkyl, A being $-CH_2-$, oxygen or nitrogen atom, $N\overbrace{A}$ forms five or six-member ring (the ring may have no substitutent or have at least one substituent selected from lower alkyl, lower alkoxy and halogen atom), or an acid salt thereof, are useful as agricultural miticides.

3 Claims, No Drawings

PYRAN DERIVATIVES

This is a division of application Ser. No. 920,937, filed Oct. 20, 1986 (and issued as U.S. Pat. No. 4,742,078), which is a continuation of application Ser. No. 614,165 filed on May 5, 1984 and now abandoned.

TECHNICAL FIELD

The invention relates to a novel pyran derivative, process for preparing the derivative and a miticide containing the derivative.

DETAILED DESCRIPTION OF THE INVENTION

The pyran derivative of the invention is represented by a general formula below.

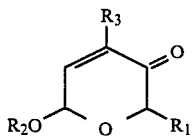

[1]

wherein $R_1$ is hydrogen, lower alkyl, cycloalkyl or phenyl, $R_2$ is alkyl having 8 to 20 carbon atoms, $R_3$ is hydrogen, halogen,

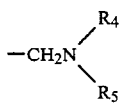

or $-CH_2N\overbrace{\phantom{xx}}A$, $R_4$ and $R_5$ being each lower alkyl or cycloalkyl, A being $-CH_2-$, oxygen or nitrogen atom, $N\overbrace{\phantom{xx}}A$ forms five or six-member ring (the ring may have no substituent or have at least one substituent selected from lower alkyl, lower alkoxy and halogen atom).

In the above general formula [1], examples of lower alkyl are methyl, ethyl, n-propyl, isopropyl, n-butyl, isobutyl, pentyl, hexyl, etc. Examples of cycloalkyl are cyclopropyl, cyclobutyl, cyclopentyl, cyclohexyl, cycloheptyl, etc. Examples of alkyl having 8 to 20 carbon atoms are octyl, decyl, undecyl, tetradecyl, octadecyl, eicosyl, etc. Halogen atoms include chlorine, bromine, etc.

It has been reported that compounds analogous to the pyran derivative of the above formula [1] of the invention were useful as intermediates of maltol derivatives [Japanese Unexamined Patent Application (KOKAI) Nos. 12,166/1977 and 18,578/1978].

The pyran derivatives of the present invention are different from the above known compounds in terms of the substituent on the pyran ring, and have acaricide action which are not disclosed in the above prior references. The present compounds are low in toxicity and are especially useful as agricultural miticides. The present invention has been accomplished by the above findings.

Representative pyran derivatives of the formula [1] having acaricide action are as follows:
6-Lauryloxy-2H-pyran-3(6H)-one
6-Lauryloxy-2-methyl-2H-pyran-3(6H)-one
6-Lauryloxy-2-ethyl-2H-pyran-3(6H)-one
6-Decyloxy-2-n-propyl-2H-pyran-3(6H)-one
6-Lauryloxy-2-n-propyl-2H-pyran-3(6H)-one
6-Cetyloxy-2-n-propyl-2H-pyran-3(6H)-one
6-Octyloxy-2-isopropyl-2H-pyran-3(6H)-one
6-Decyloxy-2-isopropyl-2H-pyran-3(6H)-one
6-Lauryloxy-2-isopropyl-2H-pyran-3(6H)-one
6-Cetyloxy-2-isopropyl-2H-pyran-3(6H)-one
6-Lauryloxy-2-cyclopropyl-2H-pyran-3(6H)-one
6-Cetyloxy-2-cyclopropyl-2H-pyran-3(6H)-one
6Lauryloxy-2-n-butyl-2H-pyran-3(6H)-one
6-Octyloxy-2-isobutyl-2H-pyran-3(6H)-one
6-Lauryloxy-2-isobutyl-2H-pyran-3(6H)-one
6-Lauryloxy-2-n-amyl-2H-pyran-3(6H)-one
6-Octyloxy-2-n-hexyl-2H-pyran-3(6H)-one
6-Lauryloxy-2-phenyl-2H-pyran-3(6H)-one
6-Octyloxy-2-cyclohexyl-2H-pyran-3(6H)-one
6-Lauryloxy-2-cyclohexyl-2H-pyran-3(6H)-one
6-Decyloxy-4-chloro-2-n-propyl-2H-pyran-3(6H)-one
6-Lauryloxy-4-bromo-2-n-propyl-2H-pyran-3(6H)-one
6-Cetyloxy-4-chloro-2-n-propyl-2H-pyran-3(6H)-one
6-Cetyloxy-4-bromo-2-n-propyl-2H-pyran-3(6H)-one
6-Octyloxy-4-chloro-2-isopropyl-2H-pyran-3(6H)-one
6-Lauryloxy-4-chloro-2-isopropyl-2H-pyran-3(6H)-one
6-Cetyloxy-4-chloro-2-isopropyl-2H-pyran-3(6H)-one
6-Cetyloxy-4-bromo-2-isopropyl-2H-pyran-3(6H)-one
6-Cetyloxy-4-chloro-2-cyclopropyl-2H-pyran-3(6H)-one
6-Cetyloxy-4-bromo-2-cyclohexyl-2H-pyran-3(6H)-one
6-Lauryloxy-4-chloro-2-isobutyl-2H-pyran-3(6H)-one
6-Lauryloxy-4-di-n-butylaminomethyl-2-n-propyl-2H-pyran-3(6H)-one
6-Cetyloxy-4-diethylaminomethyl-2-n-propyl-2H-pyran-3(6H)-one
6-Cetyloxy-4-piperidinomethyl-2-n-propyl-2H-pyran-3(6H)-one
6-Cetyloxy-4-(4-methyl)piperidinomethyl-2-n-propyl-2H-pyran-3(6H)-one
6-Octyloxy-4-di-n-butylaminomethyl-2-isopropyl-2H-pyran-3(6H)-one
6-Octyloxy-4-piperidinomethyl-2-isopropyl-2H-pyran-3(6H)-one
6-Lauryloxy-4-piperidinomethyl-2-isopropyl-2H-pyran-3(6H)-one
6-Cetyloxy-4-diethylaminomethyl-2isopropyl-2H-pyran-3(6H)-one
6-Cetyloxy-4-di-n-butylaminomethyl-2-isopropyl-2H-pyran-3(6H)-one
6-Cetyloxy-4-piperidinomethyl-2-isopropyl-2H-pyran-3(6H)-one
6-Cetyloxy-4-(4-methyl)piperidinomethyl-2-isopropyl-2H-pyran-3(6H)-one
6-Cetyloxy-4-morpholinomethyl-2-isopropyl-2H-pyran-3(6H)-one
6-Cetyloxy-4-N-methylpiperazinomethyl-2-isopropyl-2H-pyran-3(6H)-one
6-Cetyloxy-4-pyrrolidinomethyl-2-isopropyl-2H-pyran-3(6H)-one
6-Lauryloxy-4-piperidinomethyl-2-cyclopropyl-2H-pyran-3(6H)-one
6-Cetyloxy-4-piperidinomethyl-2-cyclopropyl-2H-pyran-3(6H)-one
6-Cetyloxy-4-(4-methyl)piperidinomethyl-2-cyclopropyl-2H-pyran-3(6H)-one
6-Lauryloxy-4-piperidinomethyl-2isobutyl-2H-pyran-3(6H)-one
6-Lauryloxy-4-piperidinomethyl-2-cyclohexyl-2H-pyran-3(6H)-one The present pyran derivatives of the formula [1] are prepared, for example, by the following reaction equations 1 to 3.

[Reaction equation 1]

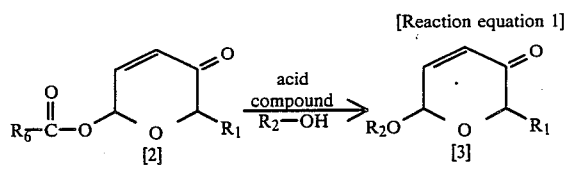

wherein $R_1$ and $R_2$ are as defined above, $R_6$ is lower alkyl group.

In the above, the starting pyran derivative [2] is a known compound and is prepared according to a disclosure in Japanese Unexamined Patent Publication (Kokai) No. 128876/1978. The reaction of the derivative [2] with the alcohol is conducted in the presence of an acid compound in a solvent. Examples of useful alcohols are octyl alcohol, 2-ethylhexyl alcohol, nonyl alcohol, decyl alcohol, lauryl alcohol, cetyl alcohol, stearyl alcohol, eicosyl alcohol, etc. Examples of useful solvents include diethyl ether, tetrahydrofuran, dioxane and like ethers, benzene, toluene, xylene and like aromatic hydrocarbons, dichloromethane, chloroform, carbon tetrachloride and like hydrocarbon halides, etc. Examples of useful acid compounds are stannic chloride, zinc chloride, boron fluoride and like Lewis acid, trifluoroacetic acid, p-toluenesulfonic acid and like organic acid, sulfuric acid, hydrochloric acid, phosphoric acid and like inorganic acid. The alcohols are used in an amount of usually about 0.5 to 3 moles, preferably about 1 to 1.2 moles per mole of the starting pyran derivative [2]. The acid compounds are used in an amount of usually about 0.001 to 0.1 mole, preferably about 0.05 to 0.1 mole per mole of the starting derivative [2]. The reaction is completed at a temperature of usually −30 to 40° C., preferably 0° C. to room temperature for about 3 to 10 hours. In the above, the present compound of the formula [1] wherein $R_3$ is hydrogen atom (compound [3]) is obtained.

[Reaction equation 2]

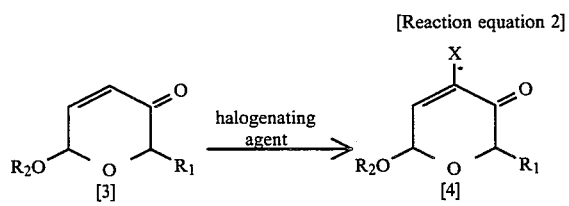

wherein $R_1$ and $R_2$ are as defined above, X is halogen atom.

In the above, the starting pyran derivative [3] is obtained according to the above reaction equation 1. The reaction of the compound [3] with a halogenating agent is conducted preferably in a solvent such as a before-mentioned hydrocarbon halide, ether, etc., at a temperature of −30 to 50° C., preferably 0° C. to room temperature for about 30 minutes to 2 hours. The reaction is completed by adding a basic compound and heating the system at a same temperature for about 1 to 3 hours. Halogenating agents include chlorine, bromine, iodine and like halogen atoms, hypochlorous acid, hypobromous acid, hypoiodous acid and like hypohalogenous acids, etc., and are used in an amount of at least one mole, preferably 1 to 1.2 moles per mole of the starting compound. Basic compounds include triethylamine, tripropylamine, pyridine and like tertiary amines, sodium hydroxide, potassium hydroxide, sodium carbonate, potassium carbonate and like inorganic bases, and are used in an amount of usually at least one mole, preferably 1 to 2 moles per mole of the starting compound. Thus, the present compound of the formula [1] wherein $R_3$ is halogen atom (compound [4]) is obtained.

[Reaction equation 3]

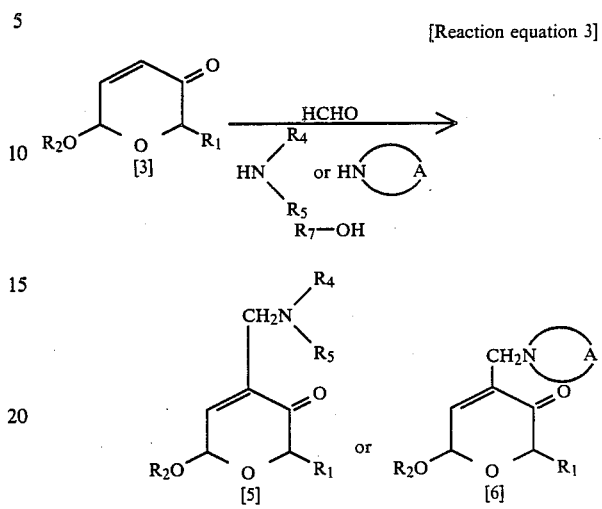

wherein $R_1$, $R_2$, $R_4$, $R_5$ and A are as defined above, $R_7$ is lower alkyl.

The aminomethylation of the compound [3], formaldehyde and amine is conducted preferably in a lower alcohol. Examples of useful lower alcohols are methanol, ethanol, propanol, butanol and the like. Each of formaldehyde and amine is used in an amount of about 0.5 to 3 moles, preferably about 1 to 1.5 moles per mole of the starting compound [3]. The reaction is conducted at a temperature of usually room temperature to 100° C., preferably about 40° to 60° C. for about 3 to 10 hours. The desired compound [5] or [6] is isolated in the form of an acid salt thereof, when desired. Thus, the present compound of the formula [1] in which $R_3$ is aminomethyl (compound [5] or [6]) is obtained.

The present compound of the formula [1] can be prepared according to the above reaction equations 1 to 3, and can easily be separated and purified by a usual method such as solvent extraction, solvent dilution, distillation, recrystallization, column chromatography, etc. The present pyran derivative is a novel compound which does not resemble commercially available miticides, and is highly estimated for totally preventing mites due to its long lasting miticide activity.

The present miticide composition contains the pyran derivative of the formula [1] as an effective component. The composition is formulated into desired preparations as similar to usual insecticides. For example, the composition can be in any of various forms such as particle, powder, emulsion, dispersion, aqueous solution, tablet, oily solution, spray, aerosol, etc., in combination with suitable solid carrier, liquid carrier, suspending agent, spreader, etc. Examples of useful carriers are clay, kaolin, bentonite, talc, terra abla, diatomaceous earth, calcium carbonate, nitrocellulose, starch, gum arabic, carbon dioxide, fluorinated hydrocarbon, water, benzene, kerosene, alcohol, acetone, xylene, methylnaphthalene, cyclohexanone, animal or vegetable fatty acid ester, etc. Examples of suspending agents and spreaders are usual surfactants such as soap, higher alcohol sulfate ester, alkylsulfonic acid salt, quaternary ammonium salt, polyalkylene oxide, etc.

The amount of the present compound of the formula [1] to be contained in the miticide of this invention can be suitably determined according to the forms used, etc. For example, in the form of dispersion or aqueous solution, the amount is usually about 0.1 to 90% by weight of the whole composition. In the form of powder or oily solution, the amount is usually about 0.1 to 10% by weight.

The present miticide composition can be applied by spreading, spraying, coating and the like to places requiring sterilization effects in the same manner as with known insecticides. The amount to be applied can be suitably determined but is usually about 0.1 to 10 kg, preferably about 0.1 to 5 kg of the effective component per one hectare for agricultural and horticultural uses. The amount can be suitably increased or decreased depending on the kinds of plants, symptoms, etc. The present miticide composition can be used in combination with other miticide, germicide, herbicide, fertilizer, soil improving agent, etc.

The invention will be described below in greater detail with reference to the following preparation examples and test examples.

PREPARATION EXAMPLE 1

In 50 ml of ethyl ether were dissolved 3.96 g of 6-acetoxy-2-isopropyl-2H-pyran-3(6H)-one and 4.84 g of cetyl alcohol with stirring. Into the solution was gradually added 0.1 ml of anhydrous stannic chloride at a temperature of 5° to 10° C. The reaction mixture was stirred at room temperature for 7 hours, washed twice with aqueous sodium hydrogencarbonate solution and once with saturated aqueous sodium chloride solution and then dried over anhydrous magnesium sulfate. By the distillation of solvent was obtained 7.0 g of 6-cetyloxy-2-isopropyl-2H-pyran-3(6H)-one [compound 1] in a yellow viscous oily form.

IR (neat, cm$^{-1}$); 1698 (C=O), 1628 (C=C)

NMR (CDCl$_3$); 0.92 (m, 6H, CH$_3$-C), 1.04 (m, 3H, CH$_3$-C), 1.24 (m, 28H, CH$_2$-C), 2.38 (m, 1H, CH-C), 3.55 (m, 2H, CH$_2$-O), 4.22 (m, 1H, CH-O), 5.20 (m, 1H, CH-O), 6.04 (m, 1H, CH=C), 6.78 (m, 1H, CH=C)

PREPARATION EXAMPLE 2

In 50 ml of carbon tetrachloride was dissolved 3.8 g of 6-cetyloxy-2-isopropyl-2H-pyran-3(6H)-one with stirring. Into the solution was gradually introduced chlorine gas (0.71 g) at a temperature below 10° C. and after the subsequent stirring for 30 minutes was added dropwise 0.8 g of pyridine maintaining the temperature below 15° C. A crystal from the reaction mixture was separated by suction filter. The filtrate was washed with 5% aqueous hydrochloric acid solution, saturated aqueous sodium hydrogencarbonate solution and saturated aqueous sodium chloride solution, and then dried over anhydrous magnesium sulfate. By the distillation of solvent was obtained 4.12 g of 6-cetyloxy-4-chloro-2-isopropyl-2H-pyran-3(6H)-one [compound 2] in a yellow viscous oily form.

IR (neat, cm$^{-1}$); 1690 (C=O), 1624 (C=C)

NMR (CDCl$_3$); 0.92 (m, 6H, CH$_3$-C), 1.04 (m, 3H, CH$_3$-C), 1.23 (m, 28H, CH$_2$-C), 2.38 (m, 1H, CH-C), 3.55 (m, 2H, CH$_2$-O), 4.22 (m, 1H, CH-O), 5.32 (m, 1H, CH-O), 7.12 (m, 1H, CH=C)

PREPARATION EXAMPLE 3

In 50 ml of methanol was dissolved 3.8 g of 6-cetyloxy-2-isopropyl-2H-pyran-3(6H)-one with stirring. Into the solution were added 1.02 g of piperidine and 1.05 g of 37% formalin solution, and the mixture was stirred at 55° to 60° C. for 7 hours. After the removal of methanol, the residue was separated by a silica gel column (developer: benzene/ethyl acetate=5/1) to give 4.62 g of 6-cetyloxy-4-piperidinomethyl-2-isopropyl-2H-pyran-3(6H)-one [compound 3] in a yellowish brown viscous oily form.

IR (neat, cm$^{-1}$); 1698 (C=O), 1628 (C=C)

NMR (CDCl$_3$); 0.90 (m, 6H, CH$_3$-C), 0.98 (m, 3H, CH$_3$-C) 1.24 (m, 28H, CH$_2$-C), 1.46 (m, 6H, CH 2-C) 2.28 (m, 4H, CH$_2$-N), 2.38 (m, 1H, CH-C) 3.0 (m, 2H, CH$_2$-N), 3.52 (m, 2H, CH$_2$-C) 4.22 (m, 1H, CH-O), 5.20 (m, 1H, CH-O), 6.68 (m, 1H, CH=C)

In the following Table 1 were given characteristics of some of compounds of the invention which were prepared in a similar manner to Preparation Examples 1 to 3. In the Table, IR is shown by (neat, cm$^{-1}$) and NMR by (CDCl$_3$, δ).

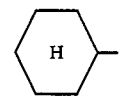

means cyclohexyl group and Et means ethyl group.

TABLE 1

| No. | Compound | Spectroscopic data |
|---|---|---|
| 4 | C$_{12}$~~~O~~O~~CH$_3$ (with C=O and CH=CH) | IR; 1698(C=O), 1628 (C=C)<br>NMR; 0.92(m, 3H, CH$_3$—C),<br>1.22(m, 3H, CH$_3$—C),<br>3.55(m, 2H, CH$_2$—O),<br>4.22(m, 1H, CH—O),<br>5.20(m, 1H, CH—O),<br>6.04(m, 1H, CH=C),<br>6.78(m, 1H, CH=C) |
| 5 | C$_{12}$~~~O~~O~~ (with C=O and CH=CH, ethyl) | IR; 1698(C=O), 1628 (C=C)<br>NMR; 0.92(m, 6H, CH$_3$—C),<br>1.24(m, 24H, CH$_2$—C),<br>3.55(m, 2H, CH$_2$—O),<br>4.22(m, 1H, CH—O),<br>5.20(m, 1H, CH—O),<br>6.04(m, 1H, CH=C),<br>6.78(m, 1H, CH=C) |

TABLE 1-continued

| No. | Compound | Spectroscopic data |
|---|---|---|
| 6 | C₁₂ chain attached via O to pyranone ring with isopropyl substituent | IR; 1698(C=O), 1628 (C=C)<br>NMR; 0.92(m, 9H, CH₃—C),<br>1.24(m, 20H, CH₂—C),<br>2.38(m, 1H, CH—C),<br>3.55(m, 2H, CH₂—O),<br>4.22(m, 1H, CH—O),<br>5.20(m, 1H, CH—O),<br>6.04(m, 1H, CH=C),<br>6.78(m, 1H, CH=C) |
| 7 | C₁₆ chain attached via O to pyranone ring with cyclopropyl substituent | IR; 1698(C=O), 1628 (C=C)<br>NMR; 0.48(m, 4H, CH₂—C),<br>0.90(m, 3H, CH₃—C),<br>1.24(m, 28H, CH₂—C),<br>1.68(m, 1H, CH—C),<br>3.55(m, 2H, CH₂—O),<br>4.22(m, 1H, CH—O),<br>5.20(m, 1H, CH—O),<br>6.04(m, 1H, CH=C),<br>6.78(m, 1H, CH=C) |
| 8 | C₈ chain attached via O to pyranone ring with cyclohexyl substituent | IR; 1698(C=O), 1628 (C=C)<br>NMR; 0.92(m, 3H, CH₃—C),<br><br>0.7–1.9(broad, 11H, cyclohexyl-H),<br><br>1.24(m, 12H, CH₂—C),<br>3.55(m, 2H, CH₂—O),<br>4.22(m, 1H, CH—O),<br>5.20(m, 1H, CH—O),<br>6.04(m, 1H, CH=C),<br>6.78(m, 1H, CH=C) |
| 9 | C₁₆ chain attached via O to pyranone ring with Cl on vinyl and propyl substituent | IR; 1690(C=O), 1624 (C=C)<br>NMR; 0.92(m, 6H, CH₃—C),<br>1.24(m, 32H, CH₂—C),<br>3.55(m, 2H, CH₂—O),<br>4.22(m, 1H, CH—O),<br>5.32(m, 1H, CH—O),<br>7.12(m, 1H, CH=C) |
| 10 | C₁₆ chain attached via O to pyranone ring with Br on vinyl and isopropyl substituent | IR; 1690(C=O), 1624 (C=C)<br>NMR; 0.92(m, 6H, CH₃—C),<br>1.04(m, 3H, CH₃—C),<br>1.23(m, 28H, CH₂—C),<br>2.38(m, 1H, CH—C),<br>3.55(m, 2H, CH₂—O),<br>4.22(m, 1H, CH—O),<br>5.32(m, 1H, CH—O),<br>7.12(m, 1H, CH=C) |
| 11 | C₁₆ chain attached via O to pyranone ring with Cl on vinyl and cyclopropyl substituent | IR; 1690(C=O), 1624 (C=C)<br>NMR; 0.48(m, 4H, CH₂—C),<br>0.90(m, 3H, CH₃—C),<br>1.24(m, 28H, CH₂—C),<br>1.68(m, 1H, CH—C),<br>3.55(m, 2H, CH₂—O),<br>4.22(m, 1H, CH—O),<br>5.32(m, 1H, CH—O),<br>7.12(m, 1H, CH=C) |

| No. | Compound | Spectroscopic data |
|---|---|---|
| 12 | 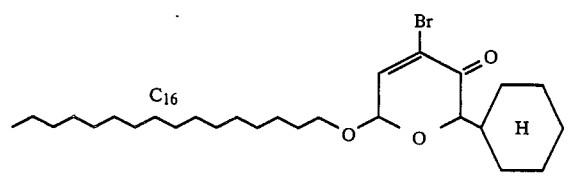 | IR; 1690(C=O), 1624 (C=C)<br>NMR; 0.92(m, 3H, CH$_3$—C),<br>0.7–1.9(broad, 11H, 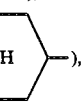),<br>1.24(m, 28H, CH$_2$—C),<br>3.55(m, 2H, CH$_2$—O),<br>4.22(m, 1H, CH—O),<br>5.32(m, 1H, CH—O),<br>7.12(m, 1H, CH=C) |
| 13 | 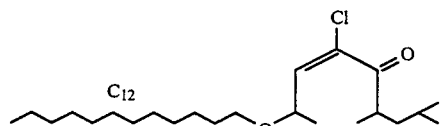 | IR; 1690(C=O), 1624 (C=C)<br>NMR; 0.94(m, 9H, CH$_3$—C),<br>1.28(m, 22H, CH$_2$—C),<br>1.70(m, 1H, CH—C),<br>3.55(m, 2H, CH$_2$—O),<br>4.22(m, 1H, CH—O),<br>5.32(m, 1H, CH—O),<br>7.12(m, 1H, CH=C) |
| 14 | 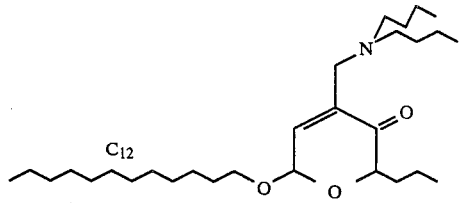 | IR; 1698(C=O), 1628 (C=C)<br>NMR; 0.94(m, 9H, CH$_3$—C),<br>1.26(m, 32H, CH$_2$—C),<br>2.32(m, 4H, CH$_2$—N),<br>3.02(m, 2H, CH$_2$—N),<br>3.53(m, 2H, CH$_2$—O),<br>4.22(m, 1H, CH—O),<br>5.20(m, 1H, CH—O),<br>6.68(m, 1H, CH=C) |
| 15 | 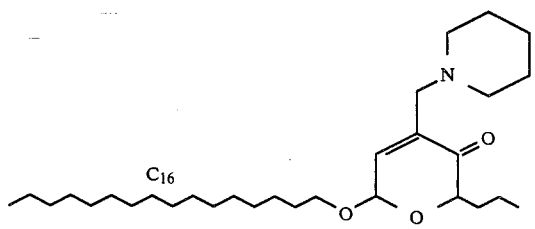 | IR; 1698(C=O), 1628 (C=C)<br>NMR; 0.92(m, 6H, CH$_3$—C),<br>1.24(m, 32H, CH$_2$—C),<br>1.46(m, 6H, CH$_2$—C),<br>2.28(m, 4H, CH$_2$—N),<br>3.0(m, 2H, CH$_2$—N),<br>3.52(m, 2H, CH$_2$—O),<br>4.22(m, 1H, CH—O),<br>5.20(m, 1H, CH—O),<br>6.68 (m, 1H, CH=C) |
| 16 | 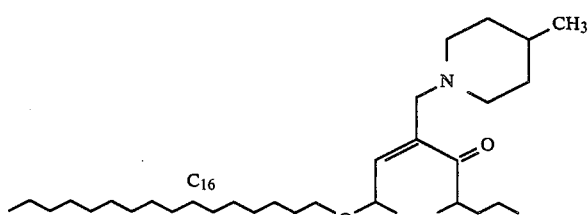 | IR; 1698(C=O), 1628(C=C)<br>NMR; 0.92(m, 9H, CH$_3$—C),<br>1.24(m, 32H, CH$_2$—C),<br>1.46(m, 5H, CH$_2$—C),<br>2.30(m, 4H, CH$_2$—N),<br>3.02(m, 2H, CH$_2$—N),<br>3.52(m, 2H, CH$_2$—O),<br>4.23(m, 1H, CH—O),<br>5.20(m, 1H, CH—O),<br>6.68(m, 1H, CH=C) |
| 17 | 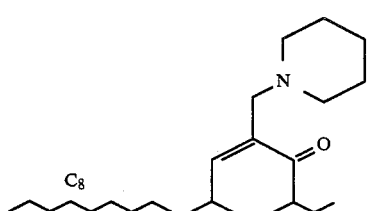 | IR; 1698(C=O), 1628(C=C)<br>NMR; 0.90(m, 6H, CH$_3$—C),<br>0.98(m, 3H, CH$_3$—C),<br>1.24(m, 12H, CH$_2$—C),<br>1.46(m, 6H, CH$_2$—C),<br>2.28(m, 4H, CH$_2$—N),<br>2.38(m, 1H, CH—C),<br>3.0(m, 2H, CH$_2$—N),<br>3.52(m, 2H, CH$_2$—O),<br>4.22(m, 1H, CH—O),<br>5.20(m, 1H, CH—O),<br>6.68(m, 1H, CH=C) |

TABLE 1-continued

| No. | Compound | Spectroscopic data |
|---|---|---|
| 18 | (C$_{12}$ chain, piperidinylmethyl substituent) | IR; 1698(C=O), 1628(C=C)<br>NMR; 0.90 (m, 6H, CH$_3$—C),<br>0.98(m, 3H, CH$_3$—C),<br>1.24(m, 20H, CH$_2$—C),<br>1.46(m, 6H, CH$_2$—C),<br>2.28(m, 4H, CH$_2$—N),<br>2.38(m, 1H, CH—C),<br>3.0(m, 2H, CH$_2$—N),<br>3.52(m, 2H, CH$_2$—O),<br>4.22(m, 1H, CH—O),<br>5.20(m, 1H, CH—O),<br>6.68(m, 1H, CH=C) |
| 19 | (C$_{16}$ chain, N(Et)$_2$ methyl substituent) | IR; 1698(C=O), 1628(C=C)<br>NMR; 0.92(m, 6H, CH$_3$—C),<br>0.98(m, 3H, CH$_3$—C),<br>1.04(m, 6H, CH$_3$—C),<br>1.24(m, 28H, CH$_2$—C),<br>2.32(m, 4H, CH$_2$—N),<br>2.38(m, 1H, CH—C),<br>3.02(m, 2H, CH$_2$—N),<br>3.52(m, 2H, CH$_2$—O),<br>4.22(m, 1H, CH—O),<br>5.20(m, 1H, CH—O),<br>6.68(m, 1H, CH=C) |
| 20 | (C$_{16}$ chain, 4-methylpiperidinylmethyl substituent) | IR; 1698(C=O), 1628(C=C)<br>NMR; 0.92(m, 12H, CH$_3$—C),<br>1.24(m, 28H, CH$_2$—C),<br>1.46(m, 5H, CH$_2$—C),<br>2.28(m, 4H, CH$_2$—N),<br>2.38(m, 1H, CH—C),<br>3.02(m, 2H, CH$_2$—N),<br>3.52(m, 2H, CH$_2$—O),<br>4.23(m, 1H, CH—O),<br>5.20(m, 1H, CH—O),<br>6.68(m, 1H, CH=C) |
| 21 | (C$_{16}$ chain, 4-methylpiperazinylmethyl substituent) | IR; 1698(C=O), 1628(C=C)<br>NMR; 0.92(m, 9H, CH$_3$—C),<br>1.24(m, 28H, CH$_2$—C),<br>2.22(s, 3H, CH$_3$—N),<br>2.28(m, 4H, CH$_2$—N),<br>2.30(m, 4H, CH$_2$—N),<br>2.38(m, 1H, CH—C),<br>3.02(m, 2H, CH$_2$—N),<br>3.52(m, 2H, CH$_2$—O),<br>4.23(m, 1H, CH—O),<br>5.20(m, 1H, CH—O),<br>6.68(m, 1H, CH=C) |
| 22 | (C$_{16}$ chain, morpholinylmethyl substituent) | IR; 1698(C=O), 1628(C=C)<br>NMR; 0.90(m, 6H, CH$_3$—C),<br>0.98 (m, 3H, CH$_3$—C),<br>1.24(m, 28H, CH$_2$—C),<br>2.38(m, 1H, CH—C),<br>2.42(m, 4H, CH$_2$—N),<br>3.08(m, 2H, CH$_2$—N),<br>3.52(m, 2H, CH$_2$—O),<br>3.65(m, 4H, CH$_2$—O),<br>4.22(m, 1H, CH—O),<br>5.20(m, 1H, CH—O),<br>6.68(m, 1H, CH=C) |
| 23 | (C$_{16}$ chain, piperidinylmethyl substituent, cyclopropyl) | IR; 1698(C=O), 1628(C=C)<br>NMR; 0.48(m, 4H, CH$_2$—C),<br>0.90(m, 3H, CH$_3$—C),<br>1.24(m, 28H, CH$_2$—C),<br>1.46(m, 6H, CH$_2$—C),<br>1.68(m, 1H, CH—C),<br>2.28(m, 4H, CH$_2$—N),<br>3.0(m, 2H, CH$_2$—N),<br>3.52(m, 2H, CH$_2$—O),<br>4.22(m, 1H, CH—O),<br>5.20(m, 1H, CH—O),<br>6.68(m, 1H, CH=C) |

TABLE 1-continued

| No. | Compound | Spectroscopic data |
|---|---|---|
| 24 | (structure) | IR; 1698(C=O), 1628(C=C)<br>NMR; 0.90(m, 3H, CH$_3^2$—C),<br>0.7–1.9(broad, 11H, cyclohexyl-H),<br>1.24(m, 20H, CH$_2$—C),<br>1.46(m, 6H, CH$_2$—C),<br>2.28(m, 4H, CH$_2$—N),<br>3.0(m, 2H, CH$_2$—N),<br>3.52(m, 2H, CH$_2$—O),<br>4.22(m, 1H, CH—O),<br>5.20(m, 1H, CH—O),<br>6.68(m, 1H, CH=C) |
| 25 | (structure) | IR; 1698(C=O), 1628(C=C)<br>NMR; 0.90(m, 3H, CH$_3$—C),<br>1.24(m, 20H, CH$_2$—C),<br>1.46(m, 6H, CH$_2$—C),<br>2.28(m, 4H, CH$_2$—N),<br>3.0(m, 2H, CH$_2$—N),<br>3.52(m, 2H, CH$_2$—O),<br>4.22(m, 1H, CH—O),<br>5.20(m, 1H, CH—O),<br>6.68(m, 1H, CH=C),<br>7.36(s, 5H, phenyl) |

TEST EXAMPLE 1

Twenty female adults of Tetranychus urticae were incubated on kidney beans (2-week-old seedlings) in each of two pots. A solution having a specified concentration was prepared by diluting a 50% emulsion containing one of the present compounds. The solution was applied to the kidney bean seedlings to sufficiently wet the leaf surfaces. The number of the survivals was counted in 3 days. The mortality was shown in Table 2. The same procedure as above was repeated with use of the other compounds. For comparison, the results with a control drug and with no drug are also shown in the Table. As control drug is used Kelthane (trade name, a product of Rohm & Haas Co., Ltd.).

TABLE 2

| Compound | Concentration of effective compound | |
|---|---|---|
| | 300 ppm | 150 ppm |
| 1 | 100 | 100 |
| 2 | 100 | 97 |
| 3 | 83 | 75 |
| 7 | 100 | 100 |
| 18 | 100 | 90 |
| Control | 100 | 75 |
| No drug | 0 | 0 |

TEST EXAMPLE 2

Female adults of Panonychus citri were incubated on leaves of bitter oranges for 2 days and allowed to lay eggs. The eggs as deposited on the leaves (50 leaves) were immersed for 10 seconds in a solution having a specified concentration and prepared by diluting 50% emulsion containing one of the present compounds and dried in air.

Thereafter, the eggs and leaves were placed in a chamber maintained at 27° C. without allowing them to dry. The number of hatched eggs was counted in 7 days to calculate the ratio of killed eggs. The same procedure as above was repeated with use of the other compounds. Table 3 shows the results with a control drug (Zardex, trade name, a product of Zoecon Co., Ltd.) and with no drug.

TABLE 3

| Compound | Concentration of effective compound | |
|---|---|---|
| | 200 ppm | 100 ppm |
| 1 | 100 | 100 |
| 3 | 100 | 90 |
| 15 | 97 | 95 |
| 18 | 100 | 97 |
| 23 | 90 | 85 |
| Control | 87 | 79 |
| No drug | 0 | 0 |

INDUSTRIAL USE

Novel pyran derivatives of the invention are useful as agricultural miticides.

We claim:

1. A pyran derivative represented by the formula

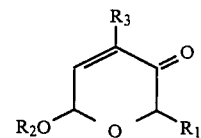

and an acid salt thereof, wherein:
$R_1$ is lower alkyl, cycloalkyl or phenyl,
$R_2$ is alkyl having 12 to 20 carbon atoms, and
$R_3$ is:
(1) the structure of formula (1)

and (2) the structure of the above formula (1) wherein at least one hydrogen is substituted by a substituent selected from the group consisting of lower alkyl, lower alkoxy and halogen.

2. A miticidal composition which comprises an inert carrier and a miticidally effective amount of a pyran derivative represented by the formula

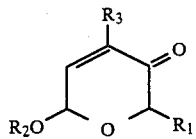

or an acid salt thereof, wherein:
$R_1$ is lower alkyl, cycloalkyl or phenyl,
$R_2$ is alkyl having 12 to 20 carbon atoms, and
$R_3$ is:
(1) the structure of formula (1)

and (2) the structure of the above formula (1) wherein at least one hydrogen is substituted by a substituent selected from the group consisting of lower alkyl, lower alkoxy and halogen.

3. A method for controlling mites, consisting essentially of the step of applying to a mite-infested area a miticidal composition which comprises a miticidally effective amount of a pyran derivative represented by the formula

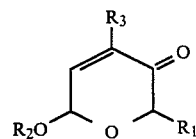

or an acid salt thereof, wherein:
$R_1$ is lower alkyl, cycloalkyl or phenyl,
$R_2$ is alkyl having 12 to 20 carbon atoms, and
$R_3$ is:
(1) the structure of formula (1)

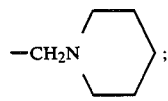

and (2) the structure of the above formula (1) wherein at least one hydrogen is substituted by a substituent selected from the group consisting of lower alkyl, lower alkoxy and halogen.

* * * * *